United States Patent [19]

Cocker et al.

[11] 4,020,058
[45] Apr. 26, 1977

[54] IMPROVEMENTS IN OR RELATING TO CEPHALOSPORIN ANTIBIOTICS

[75] Inventors: John Derek Cocker, Chalfont St. Peter; Derek Ronald Sutherland, Harrow, both of England

[73] Assignee: Glaxo Laboratories Limited, Greenford, England

[22] Filed: Dec. 16, 1974

[21] Appl. No.: 533,315

[30] Foreign Application Priority Data

Oct. 3, 1974  United Kingdom ............ 43005/74

[52] U.S. Cl. .................... 260/243 C; 424/246; 260/347.3
[51] Int. Cl.$^2$ ................ C07D 501/16
[58] Field of Search ................ 260/243 C

[56] References Cited

UNITED STATES PATENTS

| | | | |
|---|---|---|---|
| 3,546,219 | 12/1970 | Long et al. | 260/243 C |
| 3,573,294 | 3/1971 | Long et al. | 260/243 C |

FOREIGN PATENTS OR APPLICATIONS

| | | | |
|---|---|---|---|
| 2,204,060 | 8/1972 | Germany | 260/243 C |
| 2,223,375 | 11/1972 | Germany | |

*Primary Examiner*—Nicholas S. Rizzo
*Assistant Examiner*—Diana G. Rivers
*Attorney, Agent, or Firm*—Bacon & Thomas

[57] ABSTRACT

Cephalosporin antibiotics of formula

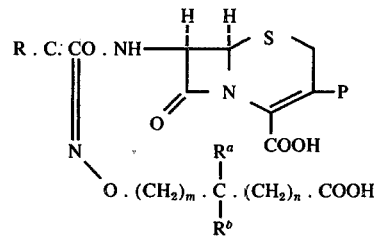

(where R is thienyl or furyl; $R^a$ and $R^b$ are each selected from hydrogen, $C_{1-4}$ alkyl, $C_{2-4}$ alkenyl, $C_{3-7}$ cycloalkyl, phenyl, naphthyl, thienyl, furyl, carboxy, $C_{2-5}$ alkoxycarbonyl and cyano, or $R^a$ and $R^b$ together with the carbon atom to which they are attached form a $C_{3-7}$ cycloalkylidene or cycloalkenylidene group; $m$ and $n$ are each 0 or 1 such that the sum of $m$ and $n$ is 0 or 1; and P is hydrogen or halogen) and their non-toxic derivatives exhibit broad spectrum antibiotic activity characterized by particularly high activity against gram negative microorganisms, including those which produce β-lactamases. The compounds, which are syn isomers or exist as mixtures of syn and anti isomers containing at least 90% of the syn isomer, have particularly high in vitro activity against strains of *Escherichia coli*, *Haemophilus influenzae* and Proteus organisms; compounds wherein at least one of $R^a$ and $R^b$ is other than hydrogen have also shown unusually high activity against Pseudomonas organisms. Important compounds of the above type include those in which the 7β-acylamido group is a syn-2-carboxymethoxy-2-(fur-2-yl)acetamido, syn-2-(2-carboxyprop-2-yloxyimino)-2-(fur-2-yl)acetamido or syn-2-(1-carboxycyclopent-1-yloxyimino)-2-(fur-2-yl)acetamido group.

7 Claims, No Drawings

IMPROVEMENTS IN OR RELATING TO CEPHALOSPORIN ANTIBIOTICS

This invention is concerned with improvements in or relating to cephalosporin compounds, and is more particularly concerned with a novel class of cephalosporin compounds possessing valuable antibiotic properties.

The cephalosporin compounds in this specification are named with reference to "cepham" after *J.Amer.-Chem. Soc.*, 1962, 84, 3400, the term "cephem" referring to the basic cepham structure with one double bond.

Cephalosporin antibiotics are widely used in the treatment of diseases caused by pathogenic bacteria in human beings and animals, for example in the treatment of diseases caused by bacteria which are resistant to other antibiotics such as penicillin compounds, and in the treatment of penicillin-sensitive patients. In many instances it is desirable to employ a cephalosporin antibiotic which exhibits activity against both gram positive and gram negative microorganisms, and a significant amount of research has been diected to the development of various types of broad spectrum cephalosporin antibiotics.

Considerable interest is currently being directed to the development of broad spectrum cephalosporin antibiotics which possess high activity against gram negative organisms. Existing commercially available β-lactam antibiotics tend to exhibit comparatively low activity against certain gram negative organisms such as Proteus organisms, which are an increasingly common source of infection in humans, and are also generally substantially inactive against Pseudomonas organisms. Several Pseudomonas organisms are resistant to the majority of existing commercially available antibiotic compounds, and the practical therapeutic applications of aminoglycoside antibiotics such as gentamicin which do exhibit Pseudomonas activity tend to be limited or complicated by the high toxicity of these antibiotics. It is well known that cephalosporin antibiotics normally exhibit low toxicity in man, so that the development of broad spectrum cephalosporin antibiotics possessing high activity against gram negative organisms such as strains of Proteus and Pseudomonas fulfils a significant need in chemotherapy.

The present invention provides 7β-acylamidoceph-3-em-4-carboxylic acid antibiotics having the general formula

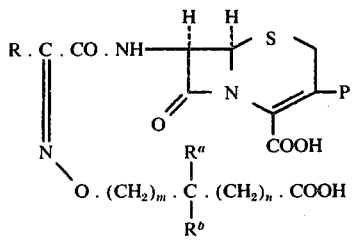

(I)

[wherein R is a thienyl or furyl group; $R^a$ and $R^b$, which may be the same or different, are each selected from hydrogen, $C_{1-4}$ alkyl (e.g. methyl, ethyl, n-propyl, isopropyl or butyl), $C_{2-4}$ alkenyl (e.g. vinyl or allyl), $C_{3-7}$ cycloalkyl (e.g. cyclopropyl, cyclobutyl, cyclopentyl or cyclohexyl), phenyl, napthyl, thenyl, furyl, carboxy, $C_{2-5}$ alkoxycarbonyl (e.g. ethoxycarbonyl) and cyano, or $R^a$ and $R^b$ together with the carbon atom to which they are attached form a $C_{3-7}$ cycloalkylidene or cycloalkenylidene group (e.g. a cyclobutylidene, cyclopentylidene or cyclohexylidene group); $m$ and $n$ are each 0 or 1 such that the sum of $m$ and $n$ is 0 or 1, and P is a hydrogen or halogen (e.g. fluorine, chlorine or bromine) atom] and non-toxic derivatives thereof, the compounds being syn isomers or existing as mixtures of syn and anti isomers containing at least 90% of the syn isomer.

These compounds exhibit broad spectrum antibiotic activity characterised by particularly high activity against gram negative microorganisms, including those which produce β-lactamases, and also possess very high stability to β-lactamases produced by a range of gram negative organisms. A characteristic feature of the compounds is their high in vitro activity against gram-negative organisms such as *Enterobacter clocae*, *Serratia marcescens* and *Klebsiella aerogenes*. The compounds have particularly high activity against strains of *Escherichia coli*, *Haemophilus influenzae* and *Proteus* organisms, e.g. strains of *Proteus morganii* and *Proteus mirabilis*. Compounds wherein at least one of $R^a$ and $R^b$ is other than hydrogen have also shown unusually high activity against *Pseudomonas* organisms, for example strains of *Pseudomonas aeruginosa*.

The compounds of the invention are defined as having the syn isomeric form as regards the configuration of the group.

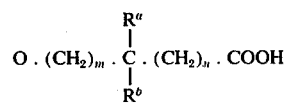

with respect to the carboxamido group. In this specification the syn configuration is denoted structurally as

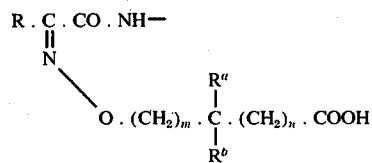

this configuration being assigned on the basis of the work of Ahmad and Spenser reported in *Can. J. Chem.*, 1961, 39, 1340. As indicated above, the compounds may exist as mixtures of syn and anti isomers provided that such mixtures contain at least 90% of the syn isomer. We prefer, however, the compounds to be syn isomers essentially free from the corresponding anti isomer.

By "non-toxic derivatives" is meant those derivatives which are physiologically acceptable in the dosage at which they are administered. Such derivatives may include, for example, salts, biologically acceptable esters, 1-oxides and solvates (especially hydrates). It will be appreciated that derivatives such as salts and esters may be formed by reaction of either or both of the carboxyl groups present in the compounds of formula I.

Non-toxic salt derivatives which may be formed from the compounds of general formula I include inorganic base salts such as alkali metal salts (e.g. sodium and potassium salts) and alkaline earth metal salts (e.g. calcium salts); organic base salts (e.g. procaine, phenylethylbenzylamine, dibenzylethylenediamine, ethanolamine, diethanolamine, triethanolamine and N-methylglucosamine salts); and, where appropriate, acid addition salts, e.g. with hydrochloric, hydrobromic, sulphuric, nitric, phosphoric, trifluoroacetic, toluene-p-sulphonic and methane sulphonic acids. The salts may also be in the form of resinates formed with, for example, a polystyrene resin or cross-linked polystyrene divinylbenzene copolymer resin containing amino or quaternary amino groups, or, where appropriate, sulphonic acid groups, or, again where appropriate, with a resin containing carboxyl groups, e.g. a polyacrylic acid resin. Use of highly soluble base salts (e.g. alkali metal salts such as the sodium salt) of compounds of formula I is generally advantageous in therapeutic applications because of the rapid distribution of such salts in the body upon administration. Where, however, insoluble salts of compounds (I) are desired in a particular application, e.g. for use in depot preparations, such salts may be formed in conventional manner, for example with appropriate organic amines.

Biologically acceptable, metabolically labile ester derivatives which may be formed from compounds of formula I include, for example, acyloxymethyl esters, e.g. lower alkanoyloxymethyl esters such as acetoxymethyl or pivaloyloxymethyl esters.

Where the group R in the above formulae is a furyl group it may be fur-2-yl or fur-3-yl and where it is a thienyl group it may be thien-2-yl or thien-3-yl.

It will be appreciated that when $R^a$ and $R^b$ in the above formulae are different, the carbon atom to which they are attached may comprise a centre of asymmetry; compounds in accordance with the invention wherein $R^a$ and $R^b$ are different may thus be diastereoisometric. The invention embraces the individual diastereoisomers of such compounds as well as mixtures thereof.

A particularly interesting class of cephalosporin antibiotics in accordance with the invention comprises compounds of general formula

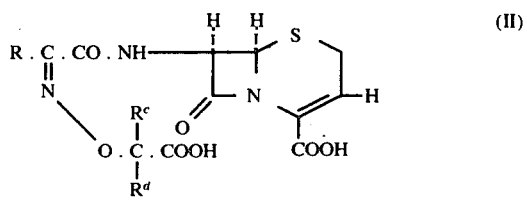

(II)

[wherein R is as hereinbefore defined, $R^c$ represents methyl, ethyl, propyl, allyl or phenyl and $R^d$ represents hydrogen, carboxyl or, more preferably, a group as defined for $R^c$; or $R^c$ and $R^d$ together with the carbon atom to which they are attached form a cyclobutylidene, cyclopentylidene or cyclohexylidene group]and non-toxic derivates thereof.

These compounds exhibit broad spectrum antibiotic activity (including very high activity against strains of Haemophilus influenzae and Proteus organisms) and high β-lactamase stability and are further characterised by particularly high in vitro activity against Pseudomonas organisms such as strains of Pseudomonas aeruginosa.

Especially preferred compounds of the above type, by virtue of their particularly high levels of activity against Proteus and Pseudomonas organisms, include the following:

[(6R,7R)-7-[2-(2-carboxyprop-2-yloxyimino)-2-(fur-2-yl) acetamido]ceph-3-em-4-carboxylic acid (syn isomer), (6R,7R)-7-[2-(1-carboxycyclopent-1-yloxyimino)-2-(fur-2-yl)acetamido]ceph-3-em-4-carboxylic acid (syn isomer), and non-toxic derivaties thereof, e.g. alkali metal salts such as the sodium or potassium salts.

A further interesting class of cephalosporin antibiotics in accordance with the invention comprises compounds of general formula

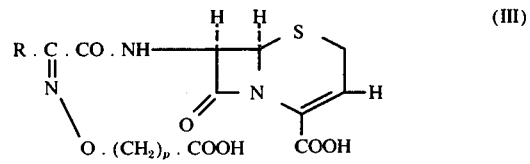

(III)

[wherein R is as hereinbefore defined and P 1 or 2] and non-toxic derivatives thereof.

These compounds exhibit broad spectrum antibiotic activity coupled with high β-lactamase stability. A characteristic feature of the compounds is their high activity against strains of Haemophilus influenzae coupled with their particularly high activity against strains of Escherichia coli and Proteus organisms.

Especially preferred compounds of the above type, by virtue of their particularly high levels of activity against Escherichia coli and Proteus organisms, include (6R,7R)-7-[2-carboxymethoxyimino-2-(fur-2-yl)acetamido]ceph-3-em-4-carboxylic acid (syn isomer), and non-toxic derivatives thereof, e.g. alkali metal salts such as the sodium or potassium salts.

The compounds according to the invention may be prepared by any convenient method, for example by techniques analagous to those described in Belgian Patent No. 783,449.

Thus according to one embodiment of the invention we provide a process for the preparation of an antibiotic compound of general formula I as hereinbefore defined or a non-toxic derivative thereof which comprises (A) condensing a compound of the formula

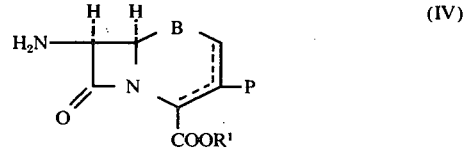

(IV)

[wherein P is as hereinbefore defined; B is > S or > S → O (α- or β-); $R^1$ represents hydrogen or a carboxyl blocking group, e.g. the residue of an ester-forming aliphatic or araliphatic alcohol or an ester-forming phenol, silanol or stannanol (the said alcohol, phenol, silanol or stannanol preferably containing 1-20 carbon atoms) or a symmetrical or mixed anhydride group derived from an appropriate acid; and the dotted line bridging the 2-, 3- and 4-positions indicates that the compound is a ceph-2-em or ceph-3-em compound] or a salt, e.g. an acid addition salt such as a hydrochloride, hydrobromide, sulphate, nitrate, phosphate, methane sulphonate or tosylate, or an N-silylated derivative thereof with an acylating agent corresponding to an acid of formula

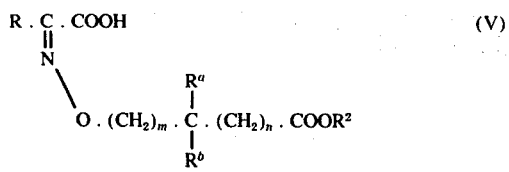

(wherein R,R$^a$,R$^b$,m and n are as hereinbefore defined and R$^2$ is a carboxyl blocking group, e.g. a group as hereinbefore defined in connection with R$^1$); whereafter, if necessary and/or desired in each instance, any of the following reactions (B) in any appropriate sequence, are carried out:

i. conversion of a $\Delta^2$ isomer into the desired $\Delta^3$ isomer,
ii. reduction of a compound wherein B is >S → O to form a compound wherein B is >S, and
iii. removal of carboxyl blocking groups; and finally (C) recovering the desired compound of formula I or a non-toxic derivative thereof, if necessary after separation of isomers.

Non-toxic derivatives of the compounds of formula I may be formed in any convenient way, for example according to methods well known in the art. Thus, for example, base salts may be formed by reaction of the cephalosporin acid with sodium 2-ethylhexanoate or potassium 2-ethylhexanoate. Biologically acceptable ester derivatives may be formed using conventional esterifying agents. 1-Oxides may be formed by treatment of the corresponding cephalosporin sulphide with an appropriate oxidising agent, for example with a peracid such as metaperiodic acid, peracetic acid, monoperphthalic acid or m-chloroperbenzoic acid, or with t-butyl hypochlorite, this last reagent conveniently being employed in the presence of a weak base such as pyridine.

Acylating agents which may be employed in the preparation of compounds of formula I include acid halides, particularly acid chlorides or bromides. Such acylating agents may be prepared by reacting an acid (V) or a salt thereof with a halogenating agent e.g. phosphorus pentachloride, thionyl chloride or oxalyl chloride. Treatment of the sodium, potassium or triethylammonium salt of the acid (V) with oxalyl chloride is advantageous in that under these conditions isomerisation is minimal.

Acylations employing acid halides may be effected in aqueous and non-aqueous reaction media, conveniently at temperatures of from −50° to +50° C, preferably, −20° to +30° C, if desired in the presence of an acid binding agent. Suitable reaction media include aqueous ketones such as aqueous acetone, esters such as ethyl acetate, halogenated hydrocarbons such as methylene chloride, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids of formula V may themselves be used as acylating agents in the preparation of compounds of formula I. Acylations employing acids (V) are desirably conducted in the presence of a condensation agent, for example a carbodiimide such as N,N'-diethyl-, dipropyl-or diisopropylcarbodiimide, N,N'-dicyclohexylcarbodiimide or N-ethyl-N'-γ-dimethylaminopropylcarbodiimide; a carbonyl compound such as carbonyldiimidazole; or an isoxazolinium salt such as N-ethyl-5-phenylisoxazolinium perchlorate. Acylation reactions of this type are desirably effected in an anhydrous reaction medium, e.g. methylene chloride, dimethylformamide or acetonitrile.

Acylation may also be effected with other amide-forming derivatives of acids of formula V such as, for example, a symmetrical anhydride or a mixed anhydride (e.g. with pivalic acid or formed with a haloformate such as a lower alkylhaloformate). The mixed or symmetrical anhydride may be generated in situ; thus, for example, a mixed anhydride may be generated using N-ethoxycarbonyl-2-ethoxy-1,2-dihydroquinoline. Mixed anhydrides may also be formed with phosphorus acids (for example phosphoric or phosphorous acids), sulphuric acid or aliphatic or aromatic sulphonic acids (for example p-toluene sulphonic acid).

It will be appreciated that in processes for the preparation of compounds of formula I wherein R$^a$ or R$^b$ represents carboxy it will be in many instances be necessary to protect the carboxy group, for example by substitution with a carboxyl blocking group, e.g. a group as hereinbefore defined in connection with R$^1$.

$\Delta^2$-Cephalosporin ester derivatives obtained in accordance with the process of the invention may be converted into the corresponding $\Delta^3$ derivative by, for example, treatment of the $\Delta^2$ ester with a base.

Ceph-2-em reaction products may also be oxidised to yield the corresponding ceph-3-em 1-oxide, for example by reaction with a peracid as mentioned previously; the resulting sulphoxide may, if desired, subsequently be reduced as described hereinafter to yield the corresponding ceph-3-em sulphide.

Where a compound is obtained in which B is >S → O this may be converted to the corresponding sulphide by, for example, reduction of the corresponding acyloxysulphonium or alkyloxylsulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of −20° to +50° C.

Where a compound of formula I is obtained as a mixture of isomers, the syn isomer may be obtained by, for example, conventional methods such as crystallisation or chromatography. Syn and anti isomers may be distinguished by appropriate techniques, e.g. by their ultraviolet spectra, by thin layer or paper chromatography or by their proton magnetic resonance spectra. Thus, for example, the p.m.r. spectra of DMSO-d$_6$ solutions of syn compounds of Formula I exhibit the doublet for the amide NH at a lower field than do similar solutions of the corresponding anti-isomers. These factors may be employed in monitoring reactions.

Starting materials of formula IV wherein P is a hydrogen atom and with the proviso that if B is >S → O then the compound is a ceph-3-em compound may, for example be prepared by the methods of Belgian Pat. No. 774,480 and French Pat. No. 2,165,834. As just defined, starting materials of general formula IV may be prepared for example by decarbonylation of a compound of formula

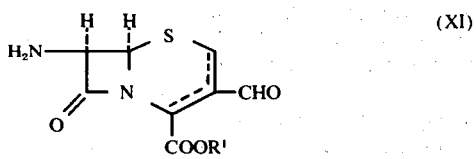

(wherein R¹ and the dotted line briding the 2,3 and 4-positions have the meanings given hereinbefore) or of a 1-oxide of a ceph-3-em compound of formula XI with a heavy metal complex which takes up carbon monoxide. Starting materials of formula IV wherein P is a halogen atom may, for example, be prepared as described in German OLS No. 2,408,686.

Acids (V) may be obtained by reacting a glyoxylic acid of formula $$R.CO.COOH \qquad (VI)$$

(where R has the above-defined meaning) or an ester thereof with a hydroxylamine derivative of formula

(where $R^a$, $R^b$, $R^2$, m and n have the above-defined meanings). The resulting acid or ester may be separated into its syn and anti isomers by, for example, crystallisation, chromatography or distillation, whereafter ester derivatives may be hydrolysed to yield the corresponding acid.

Acids (V) may also be prepared by etherification of an acid of formula

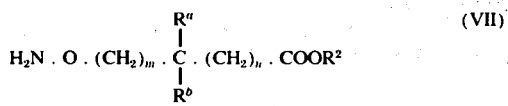

(where R has the above-defined meaning), e.g. by reaction with a compound of general formula

(wherein $R^a$, $R^b$, $R^2$, m and n are as hereinbefore defined and T is halogen such as chloro, bromo or iodo; sulphate; or sulphonate such as tosylate). Separation of isomers may be effected either before or after such etherification. The etherification reaction is desirably carried out in the presence of a base, e.g. potassium t-butoxide or sodium hydride, and is preferably conducted in an organic solvent, for example dimethyl-sulphoxide, a cyclic ether such as tetrahydrofuran or dioxan, or an N,N-disubstituted amide such as dimethylformamide. Under these conditions the configuration of the oximino group is substantially unchanged by the etherification reaction.

Derivatives of the compounds of the invention in which the carboxy substituent of the 7β-acylamido side chain is substituted by a carboxyl blocking group are also new and comprise a feature of the invention. These monoester derivatives, which may be represented by the general formula

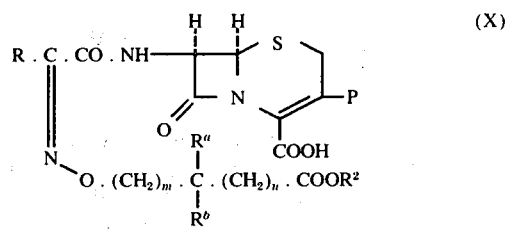

(wherein P, R, $R^a$, $R^b$, m and n are as hereinbefore defined and $R^2$ is a carboxyl blocking group such as t-butyl or diphenylmethyl), are of value as intermediates in the preparation of antibiotic compounds of general formula I. The compounds (X) may themselves exhibit antibiotic activity, although generally at a very low level when compared to corresponding compounds (I).

Carboxyl blocking groups $R^2$ and, where appropriate, $R^1$ used in the preparation of compounds of formula I or in the preparation of necessary starting materials are desirably groups which may readily be split off at a suitable stage in the reaction sequence, conveniently as the last stage. It may, however, be convenient in some instances to employ biologically acceptable, metabolically labile carboxyl blocking groups such as acyloxymethyl groups (e.g. pivaloyloxymethyl) and retain these in the final product to give a biologically acceptable ester derivative of a compound of formula I.

Suitable carboxyl blocking groups are well known in the art, a list of representative blocked carboxyl groups being included in Belgian Pat. No. 783,449. Preferred blocked carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. The carboxyl blocking group may subsequently be removed by any of the appropriate methods disclosed in the literature; thus, for example, acid or base catalysed hydrolysis is applicable in many cases, as are enzymically-catalysed hydrolyses.

The antibiotic compounds of the invention, e.g. compounds of formula I and non-toxic derivatives thereof, may be formulated for administration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

The antibiotic compounds may also be presented in a form suitable for absorption by the gastro-intestinal tract. Tablets and capsules for oral administration may be in unit dose presentation form, and may contain conventional excipients such as binding agents, for example syrup, acacia, gelatin, sorbitol, tragacanth or polyvinylpyrollidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. The tablets may be coated according to methods well known in the art. Oral liquid preparation may be in the form of, for example, aqueous or oily suspensions, solutions, emulsions, syrups or elixirs, or may be presented as a dry product for reconstitution with water or other suitable vehicle before use. Such liquid preparation may contain conventional additives such as suspending agents, for example sorbitol syrup, methyl cellulose, glucose/sugar syrup, gelatin, hydroxyethylcellulose, carboxymethyl cellulose, aluminium stearate gel or hydrogenated edible fats; emulsifying agents, for example lecithin, sorbitan mono-oleate or acacia; non-aqueous vehicles (which may include edible oils), for example almond oil, fractionated coconut oil, oily esters, propylene glycol or ethyl alcohol; and preservatives, for example methyl or propyl p-hydroxybenzoates or sorbic acid. The antibiotic compounds may also be formulated as suppositories, e.g. containing conventional suppository bases such as cocoa butter or other glyceride.

Compositions for veterinary medicine may, for example, be formulated as intramammary preparations in either long acting or quick-release bases.

The compositions may contain from 0.1% upwards, e.g. 0.1–99%, preferably from 10–60% of the active material, depending on the method of administration. When the compositions comprise dosage units, each unit will preferably contain 50–1500 mg of the active ingredient. The dosage as employed for adult human treatment will preferably range from 500 to 5000 mg per day, depending on the route and frequency of administration, although in treating Pseudomonas infections higher daily doses may be required.

The antibiotic compounds according to the invention may be administered in combination with other therapeutic agents such as antibiotics, for example penicillins, tetracyclines or other cephalosporins.

The following Examples serve to illustrate the invention.

All temperatures are in ° C. Melting points were determined in a capillary tube or on a Kofler block and are uncorrected. Those prefixed ($M_y^x$), where $x$ is the rate of heating in ° C per minute and $y$ is the insertion temperature were measured using a Mettler apparatus.

Petrol is petroleum ether b.p. 40°–60° unless otherwise stated. Dichloromethane was dried over basic alumina. Propylene oxide is DL-2-methyl-oxiran. Organic solutions were dried over sodium sulphate or magnesium sulphate before evaporation. T.l.c. is thin layer chromatography using pre-coated plates (Merck $F_{254}$, 0.25mm thick coating) which were examined under ultraviolet light at 254nm and were developed with iodine.

Preparative tlc was carried out using 20×20cm plates coated with Merck Kieselgel G or GF 254.

Paper chromatography (p.c) was carried out using Whatman No. 1 paper for propanol/water (7/3) solvent system (ascending) — System A, Whatman No. 1 paper for butanol/ethanol/water (4/1/5) upper phase (descending) — System B, and Whatman No. 1 paper for ethyl acetate/n-butanol/0.1 M sodium acetate solution (brought to pH 5 with acetic acid) (8/1/8), equilibrated at 37° with the upper phase being used as developer in descending manner in equilibrium with the lower phase, the paper being buffered to pH 6 — System C. $R_f$ values given in brackets are for cephalothin.

Proton magnetic resonance (PMR) spectra were determined at 100 MHz. Integrals were in agreement with the assignments; coupling constants (J) are in Hz, the signs not being determined.

PREPARATION 1

2-t-Butoxycarbonylmethoxyimino-2-(fur-2-yl)acetic acid (syn isomer)

The pH of a mixture of fur-2-ylglyoxylic acid (4.2g), t-butoxycarbonylmethoxyamine (4.5g) and water (50 ml) was adjusted to 5.0 with 2N sodium hydroxide solution. The resulting solution was stirred for 16 hours. The pH of the solution was increased to 7.0, and the solution was washed twice with ether. The aqueous solution was acidified to pH 1.8 under ether, and further extracted with ether. The combined ether extracts were washed (water, saturated brine), dried, and concentrated to give a solid (7.62g), which was crystallised from carbon tetrachloride to give the title compound (3.67g, 46%) m.p. 105.1°–106.2°; $\lambda_{max}$ (pH6 phosphate buffer) 277.5 nm ($\epsilon$ 16,300).

PREPARATION 2

2-(2-t-Butoxycarbonylprop-2-yloxyimino)-2-(fur-2-yl)acetic acid (syn isomer)

A solution of 2-(fur-2-yl)-2-hydroxyiminoacetic acid (syn isomer) (14.1g) in dimethyl sulphoxide (100ml) was added all at once to a magnetically stirred solution of potassium t-butoxide (22.4g) in dimethyl sulphoxide (400ml), the reaction mixture being maintained under an atmosphere of dry nitrogen. A gel was formed which, on stirring, became a finely divided, yellow solid. Stirring was continued for one hour, and then a solution of t-butyl 2-bromo-2-methylpropionate (24.0g) in dimethyl sulphoxide (50ml) was added over one hour to the reaction mixture at room temperature. After addition was complete, the resulting solution was stirred for a further hour. The reaction was poured into ice-water (1.5 liters) and acidified under ether (500ml) to pH 1.8 with concentrated hydrochloric acid. The two layers were separated, and the aqueous layer was extracted with more ether. The combined ether extracts were washed once with water, then extracted with aqueous sodium bicarbonate solution. The combined alkaline extracts were acidified under ether to pH 1.8 with concentrated hydrochloric acid, and the acid solution was extracted further with ether. The combined ether extracts were washed (water, saturated brine), dried, and concentrated to a yellow oil, which crystallised under high vacuum (22.41g, 83%), $\lambda_{max}$ (EtOH) 272.5nm ($\epsilon$ 15,400).

The above solid (22.4g) was crystallised from carbon tetrachloride (25ml) to give the title compound (16.42g, 61%), m.p. 72.5°–74.2° (73.0°).

PREPARATION 3

2-(1-t-Butoxycarbonylcyclopent-1-yloxyimino)-2-(fur-2-yl) acetic acid (syn isomer)

The dipotassium salt of 2-(fur-2-yl)-2-hydroxyiminoacetic acid (syn isomer) was generated under an atmosphere of dry nitrogen and alkylated with t-butyl 1-bromocyclopentanecarboxylate using the method of Preparation 2. The product was isolated by pouring into water, acidifying and extracting in the conventional manner, thereby yielding the title compound, m.p. 106.8°–107.3°; $\lambda_{max}$ (pH 6 buffer) 277.5 nm ($\epsilon$ 15,100); $\tau(d_6$-DMSO) values include 8.03, 8.30 (m, cyclopentyl protons) and 8.63 (C(CH$_3$)$_3$).

PREPARATION 4

2-(2-t-Butoxycarbonylprop-2-yloxyimino)-2-(fur-2-yl)acetyl chloride (syn isomer)

2-(2-t-Butoxycarbonylprop-2-yloxyimino)-2-(fur-2-yl) acetic acid (syn isomer) (715mg, 2.4mmole) was dissolved in dry dichloromethane (10ml); triethylamine (242.8mg, 0.34ml, 2.4mmole) and N,N-dimethylformamide (3 drops) were added at 0° and the solution was stirred for 15 minutes.

To this solution was added oxalyl chloride (0.33g, 2.6mmole) in dichloromethane (2ml) over a period of 20 minutes at 0°. The resulting mixture was stirred for 1 hour, evaporated and redissolved for in Example 2.

EXAMPLE 1 a. Diphenylmethyl (6R,7R)-7-[2-t-butoxycarbonylmethoxyimino-2-(fur-2-yl)acetamido]ceph-3-em-4-carboxylate(syn isomer)

Diphenylmethyl (6R,7R)-7-aminoceph-3-em-4-carboxylate (475mg, 1.3mmole) and DL-dicyclohexylcarbodiimide (295mg, 1.43 mmole) were dissolved in dry dichloromethane (20ml) at room temperature and the stirred solution was treated dropwise with a solution of 2-t-butoxycarbonylmethoxyimino-2-(fur-2-yl)acetic acid (syn isomer) (385mg, 1.43mmole) in dry dichloromethane (50ml) over 10 minutes. The solution was stirred for 2 hours at room temperature.

The dicyclohexylurea was removed by filtration and the filtrate was extracted with saturated aqueous sodium bicarbonate solution (50ml) and with brine (50ml). The resulting organic layer was evaporated to a foam, which was leached with hot ether (to remove more dicyclohexylurea), and the ether-soluble material was purified on preparative t.l.c. plates using benzene:acetone = 8:1 as eluant. The product was extracted from the plates with ethyl acetate and the solution was evaporated to a foam. The foam was stirred with diisopropyl ether to give the title ester as a powder (680mg, 85%); m.p. 90°–92°; $[\alpha]_D^{23}$ +91° (c 0.07, Me$_2$CO); $\lambda_{max}$(EtOH) 277nm (E$_{1cm}^{1\%}$ 263); tlc, R$_f$ 0.80 (benzene:acetone = 5:1). IR and PMR spectra confirmed the structure as that of the title ester.

b. (6R,7R)-7-[2-Carboxymethoxyimino-2-(fur-2-yl)acetamido]ceph-3-em-4-carboxylic acid (syn isomer)

Diphenylmethyl (6R,7R)-7-[2-t-butoxycarbonylmethoxyimino-2-(fur-2-yl)acetamido]ceph-3-em-4-carboxylate(syn isomer) (500mg, 0.8mmole) was stirred in trifluoroacetic acid (4ml) and anisole (6ml) at room temperature for 15 minutes. The red solution was poured into aqueous saturated sodium bicarbonate solution (40ml) and ethyl acetate (50ml) and the pH was adjusted to 7.5 with 2N-sodium hydroxide solution and solid sodium bicarbonate.

The aqueous layer was covered with ethyl acetate, and adjusted to pH 1.5 with concentrated hydrochloric acid. The aqueous layer as separated, washed with ethyl acetate, and the organic layers were combined. Evaporation of the ethyl acetate fraction afforded an oil, which was stirred in trifluoroacetic acid (4ml) and anisole (1ml) for 40 minutes. The mixture was evaporated and the residue was triturated with ether and petrol to give the title acid as a powder (236mg, 75%); m.p. 135° (decomp); $[\alpha]_D$ +84.2°(c 0.2, 5% sodium bicarbonate); $\lambda_{max}$(pH6 phosphate buffer) 281.5nm (E$_{1cm}^{1\%}$ 343); $\nu_{max}$(Nujol) 3700 to 2150 (bonded — OH), 3240(NH), 1774($\beta$-lactam), 1722(CO$_2$H), 1676 and 1540cm$^{-1}$(CONH); $\tau$(DMSO-d$^6$) 0.19(d, J 8Hz, —CON<u>H</u>), 2.11, 3.21, and 3.31(m, furyl protons), 3.49(m, C-3(H)), 4.08(dd, J5 and 8Hz, C-7 (H)), 4.82(d, J5Hz, C-6(H)), 5.31(s, —O<u>CH</u>$_2$CO$_2$H), and ca 6.4 (collapsed ABq, C-2(H)); p.c.-system A, R$_f$ 0.75(0.28).

EXAMPLE 2 a. Diphenylmethyl (6R,7R)-7-[2-(2-t-butoxycarbonylprop-2-yloxyimino)-2-(fur-2-yl)acetamido]ceph-3-em-4-carboxylate (syn isomer)

A solution of diphenylmethyl (6R,7R)-7-aminoceph-3-em-4-carboxylate, p-toluenesulphonic acid salt (1.076g, 2mmole) in dry dichloromethane (20ml), triethylamine (0.84ml, 6mmole), propylene oxide (0.28ml, 4mmole) and N,N-dimethylacetamide (4 drops) at 0° was treated dropwise with a solution of the acid chloride prepared as described Preparation 4. Methanol (4ml) was added and the mixture was stirred for 5 minutes. The solution was poured into aqueous saturated sodium bicarbonate solution (50ml). The organic layer was separated and the bicarbonate phase extracted with dichloromethane.

The organic phases were combined, dried, and evaporated to a foam. The foam was dissolved in dichloromethane and purified on preparative tlc plates with benzene:acetone = 5:1 as eluant.

The band containing the product was extracted with ethyl acetate and the solution was evaporated to dryness to yield the title ester as a foam (620mg, 48%); $[\alpha]_D^{24}$ +54.9° (c 1.0, CHCl$_3$); $\lambda_{max}$(EtOH) 275nm (E$_{1cm}^{1\%}$ 275); tlc, R$_f$ 0.58(toluene: ethyl acetate = 5:1). IR and PMR spectra confirmed the structure as that of the title ester.

b. (6R,7R)-7-[(2-Carboxyprop-2-yloxyimino)-2-(fur-2-yl) acetamido]ceph-3-em-4-carboxylic acid (syn isomer)

Diphenylmethyl (6R,7R)-7-[2-t-butoxycarbonylprop-2-yloxyimino)-2-(fur-2-yl)acetamido]ceph-3-em-4-carboxylate (syn isomer) (400mg, 0.62mmole) was stirred with anisole (4ml) and treated with trifluoroacetic acid (3ml). The solution was stirred for 15 minutes at room temperature and concentrated in vacuo to ca. 4ml. The residual oil was partitioned between ethyl acetate (50ml) and saturated aqueous sodium bicarbonate solution (50 ml). The ethyl acetate layer was extracted with further saturated aqueous sodium bicarbonate solution (30ml), and the aqueous layers were combined and extracted with ethyl acetate (50ml) and with ether (50ml). The basic aqueous layers were covered with fresh ethyl acetate and the pH was adjusted to 2.0 with concentrated hydrochloric acid. The acidic aqueous layer was extracted with ethyl acetate (2×75ml), and the ethyl acetate layers were combined, washed with brine (50ml), and dried. Evaporation gave an oil which was stirred with anisole (1ml) and trifluoroacetic acid (3ml) for 30 minutes at room temperature. The reaction mixture was concentrated in vacuo to an oil, which was repeatedly triturated with ether and cyclohexane to give the title acid as a colourless powder (226mg, 86%); m.p. 150°; $[\alpha]_D^{23}$ +113° ($c$ 0.1, 5% sodium bicarbonate solution); $\lambda_{max}$ (pH6 phosphate buffer) 279.5nm ($E_{1cm}^{1\%}$ 345); $\nu_{max}$(Nujol) 3650 to 2100 (bonded OH), 1777($\beta$-lactam), 1720($CO_2H$) and 1683 and 1534 cm$^{-1}$ (CONH); $\gamma$(DMSO-d$^6$)0.41(d,J8Hz,CONH), 2.18, 3.29, and 3.37 (m, furyl protons), 3.50(m, C-3(H)), 4.09(dd, J5 and 8Hz, C-7(H)), 4.82(d,J 5Hz, C-6(H)), 6.2 to 6.5(collapsed ABq, C-2(H)), and 8.5(s, —OC($\underline{CH}_3$)$_2CO_2H$); p.c. — system B, R$_f$ 0.1(0.38).

EXAMPLE 3 a. Diphenylmethyl (6R,7R)-7-[-2-(1-t-butoxycarbonylcyclopent-1-yloxyimino)-2-(fur-2-yl)acetamido]ceph-3-em-4-carboxylate (syn isomer)

A solution of diphenylmethyl (6R,7R)-7-aminoceph-3-em-4-carboxylate (1.1g, 3mmole) and DL-dicyclohexylcarbodiimide (680mg, 3.3mmole) in dry dichloromethane (30ml) was treated dropwise with 2-(1-t-butoxycarbonylcyclopent-1-yloxyimino)-2-(fur-2-yl)acetic acid (syn isomer) (1.07g, 3.3mmole) in dry dichloromethane (40ml) over 25 minutes. The solution was stirred at room temperature for 3 hours.

The precipitated dicyclohexylurea was removed by filtration, and the filtrate was washed with saturated sodium bicarbonate solution (2×50ml), water (50ml) and brine (30ml). On evaporation the organic layer afforded an oil, which was purified by preparative tlc with benzene: acetone = 7:1 as eluant to give the title ester as a powder (1.1g, 54%). A further, less pure crop from the plates was rechromatographed under the same conditions as before to give a further 100mg (5%) of product; m.p. 85°–88°; $[\alpha]_D^{23}$ +43.2° ($c$ 0.1, CHCl$_3$); $\lambda_{max}$(EtOH) 277nm ($E_{1cm}^{1\%}$ 258); tlc, R$_f$ 0.70 (toluene:acetone = 5:1). IR and PMR spectra confirmed the structure as that of the title ester.

b. (6R,7R)-7[2-(1-Carboxycyclopent-1-yloxyimino)-2-(fur-2-yl)acetamido]ceph-3-em-4-carboxylic acid (syn isomer)

The diphenylmethyl ester prepared in (a) above (1g, 1.49 mmole) was stirred in anisole (6ml) and trifluoroacetic acid (4ml) at room temperature for 20 minutes. The solution was concentrated in vacuo to ca. 6ml and poured into ethyl acetate (40ml) and saturated aqueous sodium bicarbonate solution (40ml). The organic layer was extracted with more aqueous bicarbonate (40ml), and the aqueous fractions were combined and washed with ethyl acetate (30ml) and ether (50ml).

The alkaline solution was covered with ethyl acetate (100ml) and adjusted to pH2 with concentrated hydrochloric acid. The aqueous layer was extracted with ethyl acetate (2×70ml) and the organic layers were combined and dried.

Evaporation of the solvent yielded an oil which was stirred with anisole (1ml) and trifluoroacetic acid (4ml) at room temperature for 35 minutes. The reaction mixture was subjected to similar treatment as above to yield an oil, which was dissolved in ethyl acetate and poured into petrol to yield a powder (ca. 560mg). This powder was dissolved in saturated aqueous sodium bicarbonate solution (60ml), clarified with charcoal and extracted with ethyl acetate (50ml).

The basic aqueous layer was adjusted to pH 2 with concentrated hydrochloric acid and extracted with ethyl acetate (2×100ml).

The organic extract was washed with brine (50ml) and evaporated to dryness to yield the title acid as a powder (350 mg, ca. 52%); m.p. 120°–135°(decomp); $[\alpha]_D^{23}$ +162° ($c$ 0.01, 5% aqueous NaHCO$_3$); $\lambda_{max}$(pH6 phosphate buffer) 283nm ($E_{1cm}^{1\%}$ 307); $\nu_{max}$(Nujol) 3700 to 2100 (bonded —OH, NH, H$_2$O), 1775($\beta$-lactam), 1710(CO$_2$H), 1680 and 1528cm$^{-1}$ (CONH); $\tau$(DMSO-d$^6$) 0.37(d, J 8Hz,CONH), 2.10, 3.24, 3.31 (m, furyl protons), 3.45(m, C-3(H)), 4.05(dd, J5 and 8Hz, C-7(H)), 4.80(d, J 5Hz, C-6(H)), 6.2 to 6.6(collapsed ABq, C-2(H)) and 7.9 and 8.25(2×broad s, cyclopentyl protons); p.c.—system B, R$_f$ 0.16(0.38).

EXAMPLE 4 a. Diphenylmethyl (6R,7R)-7-[2-(2-t-butoxycarbonylprop-2-yloxyimino)-2-(fur-2-yl)acetamido]-3-chloroceph-3-em-4-carboxylate (syn isomer)

Diphenylmethyl (6R,7R)-7-amino-3-chloroceph-3-em-4-carboxylate, hydronitrate salt (507 mg, 1.1 mmole) was stirred in a two phase system of dichloromethane (20 ml) and aqueous sodium bicarbonate (20 ml) at ca 22° for 10 minutes. The aqueous phase was washed with dichloromethane and the organic extracts were combined, washed with brine and dried. The resulting solution was stirred with 2-(t-butoxycarbonylprop-2-yloxyimino)-2-(fur-2-yl)acetic acid (syn isomer) (371 mg, 1.24 mmoles) and DL-dicyclohexylcarbodiimide (287 mg, 1.39 mmoles) for 30 minutes. After concentration of the reaction mixture to ca 5 ml, dicyclohexylurea was filtered off and the solution was evaporated to dryness to yield a yellow foam (661 mg) which was adsorbed on silica plates. Elution with benzene: ethyl acetate (5:1) gave the title ester as a white foam (575 mg, 78%); $[\alpha]_D^{23}$ + 87.6° ($c$ 0.232, CHCl$_3$); $\lambda_{max}$ (EtOH) 277.5 nm ($\epsilon$ 18,300); R$_f$ 0.80 (benzene; ethyl acetate = 3:1). IR and PMR spectra confirmed the structure as that of the title ester.

b. (6R,7R)-7-[2-(2-Carboxyprop-2-yloxyimino)-2-(fur-2-yl)acetamido]-3-chloroceph-3-em-4-carboxylic acid (syn isomer)

A solution of the product of (a) above (1.18 g, 1.73 mmoles) in trifluoroacetic acid (4.8 ml) and anisole (6 ml) was allowed to stand at ca 22° for 5 minutes. The solvents were removed in vacuo and an ethereal solution of the gum so obtained was precipitated from petrol (b.p. 60°–80°). T.l.c. and IR evidence suggested that deprotection was incomplete, so the precipitate was again treated with trifluoroacetic acid (2 ml) and anisole (2.5 ml) for 30 minutes, whereafter the work up described above was repeated to give the title acid as an amorphous solid (552 mg, 69%); m.p. ($M_{80}^2$) 97°; $[\alpha]_D^{23}$ + 92.5° (c 0.244, $CHCl_3$); $\lambda_{max}$ (EtOH) 272.5 nm ($\epsilon$ 16,600); $\nu_{max}$ (Nujol) 3500 ($H_2O$), 3250 (NH), 2600 and 1720 ($CO_2H$), 1780 ($\beta$-lactam), 1670 and 1540 $cm^{-1}$ (CONH); $\tau$ (DMSO-$d^6$) 0.34 (d, J 8 Hz, CON$\underline{H}$), 2.17 and 3.33 (m, furyl protons), 4.11 (dd, J 4 and 8 Hz, C-7(H)), 4.69 (d, J 4 Hz, C-6(H)), 5.98 and 6.31 (ABq, J 18 Hz, C-2(H)) and 8.51 (s, —OC(C$\underline{H}_3$)$_2$$CO_2H$); p.c.—system C, $R_f$ 0.19.

We claim:

1. A compound selected from the group consisting of a cephalosporin antibiotic of the formula:

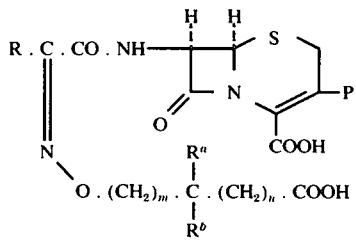

(I)

wherein R is thienyl or furyl; $R^a$ and $R^b$ are each hydrogen, $C_{1-4}$ alkyl, $C_{2-4}$ alkenyl, $C_{3-7}$ cycloalkyl, phenyl, naphthyl, thienyl, furyl, carboxy, $C_{2-5}$ alkoxycarbonyl or cyano, or $R^a$ and $R^b$ together with the carbon atom to which they are attached form a $C_{3-7}$ cycloalkylidene or cycloalkenylidene group; m and n are each 0 or 1 such that the sum of m and n is 0 or 1; and P is hydrogen, or the physiologically acceptable salts, esters, 1-oxides and solvates thereof.

2. The compound of claim 1 which is (6R,7R)-7-[2-(2-carboxyprop-2-yloxyimino)-2-(fur-2-yl) acetamido]ceph-3-em-4-carboxylic acid (syn isomer).

3. The compound of claim 1 which is (6R,7R)-7-[2-(1-carboxycyclopent-1-yloxyimino)-2-(fur-2-yl) acetamido]ceph-3-em-4-carboxylic acid (syn isomer).

4. The compound of claim 1 which is (6R,7R)-7-[2-carboxymethoxyimino-2-(fur-2-yl) acetamido]ceph-3-em-4-carboxylic acid (syn isomer).

5. A compound according to claim 1 which is a sodium or potassium salt of a compound of formula I.

6. A compound of formula:

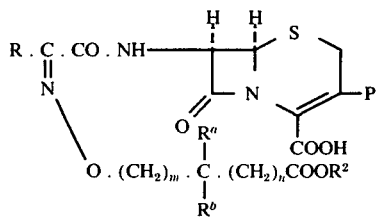

wherein R is thienyl or furyl; $R^a$ and $R^b$ are each hydrogen, $C_{1-4}$ alkyl, $C_{2-4}$ alkenyl, $C_{3-7}$ cycloalkyl, phenyl, naphthyl, thienyl, furyl, carboxy, $C_{2-5}$ alkoxycarbonyl, or cyano, or $R^a$ and $R^b$ together with the carbon atom to which they are attached form a $C_{3-7}$ cycloalkylidene or cycloalkenylidene group; m and n are each 0 or 1 such that the sum of m and n is 0 or 1; $R^2$ is a blocked carboxy group; and P is hydrogen, or physiologically acceptable salts, esters, 1-oxides and solvates thereof.

7. The compound of claim 1 which is the syn isomer or a mixture of syn and anti isomers containing at least 90% of the syn isomer.

* * * * *